(12) United States Patent
Zhang et al.

(10) Patent No.: US 7,964,756 B2
(45) Date of Patent: Jun. 21, 2011

(54) PROCESS FOR ABSORBING METHYLACROLEIN WITH IONIC LIQUID

(75) Inventors: Suojiang Zhang, Beijing (CN); Qiong Chen, Beijing (CN); Ruiyi Yan, Beijing (CN); Lei Wang, Beijing (CN); Yuhuan Chen, Beijing (CN); Xiaoliang Yuan, Beijing (CN)

(73) Assignee: Institute of Process Engineering, Chinese Academy of Sciences, Beijing (CN)

( * ) Notice: Subject to any disclaimer, the term of this patent is extended or adjusted under 35 U.S.C. 154(b) by 119 days.

(21) Appl. No.: 12/529,906

(22) PCT Filed: Mar. 10, 2008

(86) PCT No.: PCT/CN2008/000479
§ 371 (c)(1), (2), (4) Date: Sep. 3, 2009

(87) PCT Pub. No.: WO2008/110071
PCT Pub. Date: Sep. 18, 2008

(65) Prior Publication Data
US 2011/0021846 A1 Jan. 27, 2011

(30) Foreign Application Priority Data

Mar. 12, 2007 (CN) .......................... 2007 1 0064330

(51) Int. Cl.
*C07C 45/80* (2006.01)
(52) U.S. Cl. ....................................... 568/492
(58) Field of Classification Search ................... 568/492
See application file for complete search history.

(56) References Cited

U.S. PATENT DOCUMENTS

| | | | |
|---|---|---|---|
| 2,514,966 A | 7/1950 | Pierotti et al. | |
| 3,957,880 A | 5/1976 | Sato et al. | |
| 5,356,460 A | 10/1994 | Vogel et al. | |
| 5,969,178 A | 10/1999 | Okamoto et al. | |

FOREIGN PATENT DOCUMENTS

CN 1709553 A 12/2005

*Primary Examiner* — Sikarl A Witherspoon
(74) *Attorney, Agent, or Firm* — Knobbe, Martens, Olson & Bear, LLP

(57) ABSTRACT

Disclosed is a process for absorbing methylacrolein, characterized in that it absorbs methylacrolein by an absorbent comprising an ionic liquid. The absorbent can absorb methylacrolein effectively, and it is easy to be separated from methylacrolein, regenerated and recycled. It is a green absorbent. The technique is a green methylacrolein absorbing and separating technique.

3 Claims, 1 Drawing Sheet

PROCESS FOR ABSORBING METHYLACROLEIN WITH IONIC LIQUID

This application is U.S. National Phase of International Application PCT/CN2008/000479, filed Mar. 10, 2008 designating the U.S., and published in a language other than English as WO 2008/110071 on Sep. 18, 2008.

FIELD OF THE INVENTION

The present invention belongs to a technical field of gaseous product absorption, and specifically, relates to a new process for absorbing methylacrolein.

BACKGROUND OF THE INVENTION

Methyl methacrylate (MMA) as an important organic chemical product is the most primary polymerization monomer for acrylic resin plastic and has a very wide application. In China, the current process for producing methyl methacrylate is conventional acetone-cyanogen-alcohol process (ACH process). Though the ACH process is a well-established process, it has disadvantages such as high toxicity, virulent chemicals and strong acids used are harmful to environment and human beings. Accordingly, new alternative process routes have been developed, wherein a process route for preparing MMA by using $C_4$ derivatives as raw material is mostly competitive. Comparing with other methods, the method for producing MMA by using $C_4$ derivatives has the characteristics of low cost, less pollution, good economy benefit or the like. The process route for producing MMA by using $C_4$ derivatives is as follows: isobutylene (tert-butanol)→methylacrolein→methacrylic acid→methyl methacrylate, or isobutylene (tert-butanol)→methylacrolein→methyl methacrylate. Methylacrolein is produced from a mixing gas of isobutylene, oxygen gas, nitrogen gas, and steam under the effect of a catalyst. The reaction product should be purified before subjecting to a one-step oxidation and esterification reaction of methylacrolein.

U.S. Pat. No. 3,957,880 provides a method for absorbing methylacrolein with ethanol, and then performing extraction and rectification using water as an extracting agent. However, water and methylacrolein tend to form an azeotrope, which cannot satisfy the demand of the second step, that is, the oxidation and esterification reaction of methylacrolein. U.S. Pat. No. 2,514,966 provides a method for absorbing methylacrolein with water. However, because the solubility of methylacrolein in water is relatively low, a great deal of water is required to absorb methylacrolein. Therefore, this method will cause water resource waste. Additionally, the obtained product also tends to form an azeotrope which is difficult to be further purified. U.S. Pat. No. 5,969,178 reports a four-column combination process of water washing, methanol drying, methanol absorption and rectification recovery which makes use of a great deal of methanol. It will cause largely waste to use methanol as an absorbent because methanol has a high volatility. Furthermore, methanol is harmful to human beings and tends to cause environmental pollution.

Therefore, it is demanded to find a recyclable and environmental friendly absorbent which can not only absorb methylacrolein effectively, but also be separated from methylacrolein easily. Ionic liquid is a green absorbent exactly satisfying the above demands.

Ionic liquid is a substance entirely consisted of a specific cation and an anion, which is in liquid state at or near room temperature. Comparing with a traditional liquid substance, the ionic liquid has particular physicochemical properties which make it more applicable to be an adsorbing solvent for methylacrolein than methanol or water:

(1) The ionic liquid has a larger solubility for the component to be separated (methylacrolein) in the mixing gas.

(2) Some types of the ionic liquids have small solubilities for other gas components except methylacrolein in the mixing gas, that is, they have higher adsorption selectivity.

(3) The ionic liquid is very low or almost zero in terms of vapor pressure, therefore, the loss caused by volatilization during adsorption and regeneration is tiny.

(4) The ionic liquid has excellent chemical stability, and furthermore, it is nontoxic and nonflammable.

DISCLOSURE OF THE INVENTION

The invention provides a process for absorbing methylacrolein, in which methylacrolein is absorbed with an absorbent comprising an ionic liquid.

Particularly, the invention relates to the following aspects.

A first aspect is a process for absorbing methylacrolein, characterized by absorbing methylacrolein with an absorbent comprising an ionic liquid.

A second aspect is the process according to the first aspect, wherein the absorbent is a pure ionic liquid, a mixture of an ionic liquid and an alcohol, a mixture of an ionic liquid and water, or a mixture of an ionic liquid, water and an alcohol.

Generally, the ionic liquid itself has a relative high viscosity which is unfavorable for the absorption operation. However, a composite absorbent formed by adding water or an alcohol thereto has a relative low viscosity and good absorption effect. Therefore, the disadvantage due to high viscosity of the pure ionic liquid absorbent can be overcome and simultaneously excellent absorption effect can be obtained by utilizing a mixture of an ionic liquid and an alcohol, a mixture of an ionic liquid and water, or a mixture of an ionic liquid, water and an alcohol.

A third aspect is the process according to the first aspect or the second aspect, wherein the ionic liquid is selected from the group consisting of alkyl quaternary ammonium salts, alkyl quaternary phosphonium salts, N-alkyl substituted pyridiniums, N,N'-dialkyl substituted imidazoliums and mixtures thereof.

Ionic liquid is a salt consisted of a specific cation and an anion, which is in liquid state at or near room temperature. At present, it has been reported that hundreds of types of ionic liquids have been synthesized. Generally, the cations therein are classified into the following 4 types: alkyl quaternary ammonium ions, $[NR_xH_{4-x}]^+$; alkyl quaternary phosphonium ions, $[PR_xH_{4-x}]^+$; N,N'-dialkyl substituted imidazolium ions, $[RR'im]^+$; N-alkyl substituted pyridinium ions, $[RP_y]^+$. The ordinary anions are mainly classified into two types: the simple inorganic ions such as $Cl^-$, $Br^-$, $I^-$, $[NO_3]^-$, $[SO_4]^{2-}$, and $[ClO_4]^-$; the organic ions and complex ions such as $AlCl_4^-$, $[BF_4]^-$, $[PF_6]^-$, $[CF_3COO]^-$, $[CF_3SO_3]^-$, $[(CF_3SO_2)_2N]^-$, and $[SbF_6]^-$.

The process of the invention utilizes a non-volatile ionic liquid as an absorbent, which increases the adsorption efficiency. Simultaneously, this absorbent is regenerative in a simple process, recyclable and environment-friendly.

Figure 1:
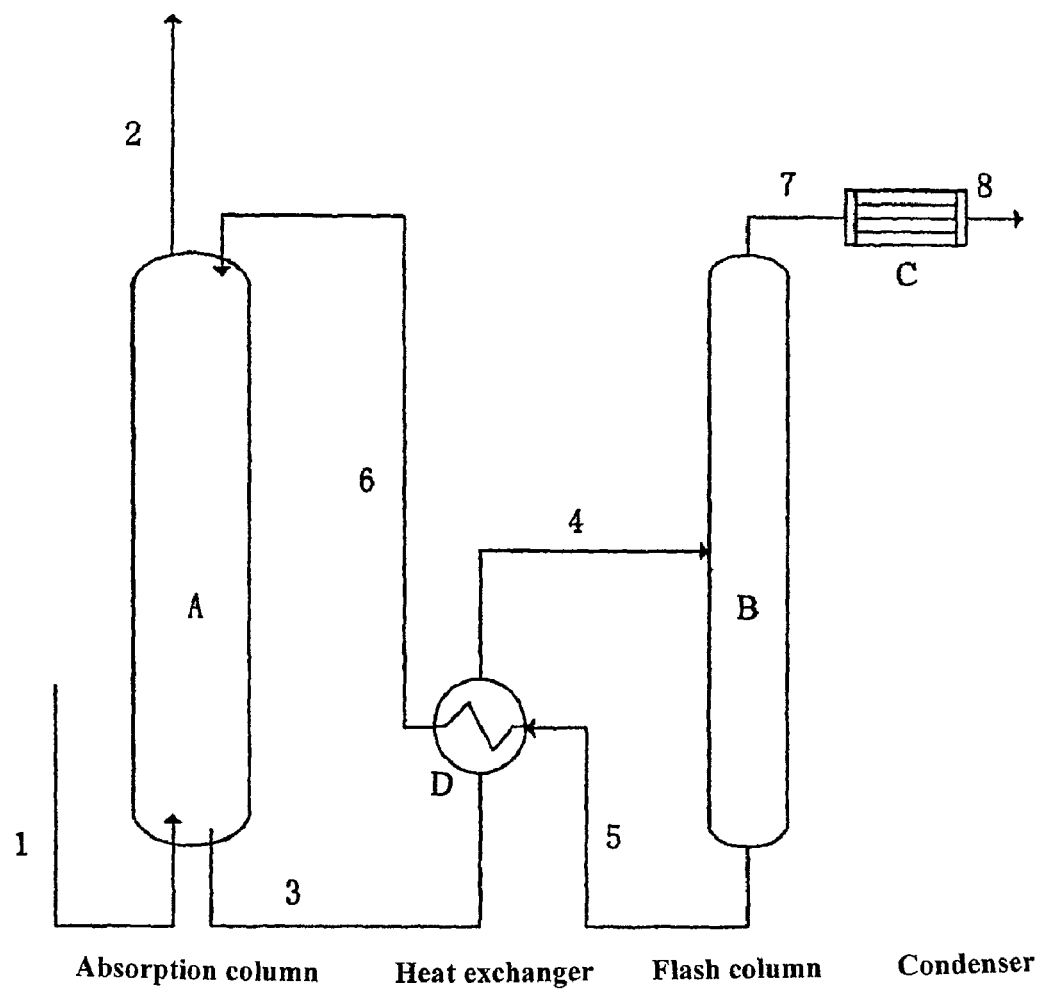
FIG. 1 is a schematic flow diagram for the process of the invention.

Wherein:

1 is a mixing gas containing methylacrolein, 2 is a discharged gas after absorption, 3, 4 are mixtures of a solvent and methylacrolein after absorption, 5, 6 are regenerated solvents, 7, 8 are methylacrolein, A is an absorption column, B is a flash column, C is a condenser, D is a heat exchanger.

SPECIFIC MODE OF CARRYING OUT THE INVENTION

FIG. 1 is a typical process flow chart of the process for absorbing methylacrolein gas according to the present invention. A one-stage reaction product gas stream containing methylacrolein gas firstly is entered into a deep cooling zone, and then entered into an absorption zone via line 1. The absorption zone includes a gas-liquid contacting apparatus which can be either an absorption column in a manner of bubbling absorption or an absorption column comprising column trays or fillers as well. In the absorption zone, the typical operating temperature is 5-15° C. and the pressure is normal pressure or low pressure.

In the absorption zone, the feed gas stream introduced via line 1 is contacted with an absorbent to remove methylacrolein gas in the feed gas stream, and resultant gas stream is discharged via line 2 from the absorption zone and returned to the one-stage reaction. The methylacrolein-enriched absorbent is discharged via line 3 from the absorption zone.

The methylacrolein-enriched absorbent can be passed through one or more desorption zones, one of which is shown in FIG. 1. Almost all of the absorbed methylacrolein gas is separated from the absorbent and discharged via line 7, and then it is condensed.

Via line 8, the methylacrolein-enriched absorbent is entered into a regeneration zone where the methylacrolein still resided in the absorbent is desorbed. Because the ionic liquid has a feature that the vapor pressure thereof is almost zero, if only an ionic liquid is used as an absorbent without mixing with other solvent, the regeneration of the absorbent can be carried out by a heating method. If an absorbent composition prepared by mixing an ionic liquid with other solvent is used as an absorbent, a regeneration process for the traditional solvent can be utilized in the regeneration zone.

After the methylacrolein-enriched absorbent is regenerated, it is returned to the absorption zone. Generally, the regenerated absorbent is cooled before entering into the absorption zone. To those persons skilled in the art, the cooling of the regenerated absorbent can be performed using a normal apparatus.

The methylacrolein gas in the gas stream is removed by contacting with the absorbent or absorbent composition of the present invention. The used absorbent or absorbent composition, that is, the methylacrolein-enriched absorbent or absorbent composition, is subjected to regeneration to remove all of or parts of the absorbed methylacrolein, and then recycled to the absorption step.

The absorbent of the present invention has been improved in many absorption performances, including improved absorption efficiency, simplified adsorption process, recyclability of absorbent or the like. It is obvious that the same mass of methylacrolein can be absorbed in high efficiency by the absorbent or absorbent composition of the present invention. In the case that the same mass of methylacrolein is removed by the absorbent or absorbent composition at a low recycle amount, the sizes, costs and the correlative operating expenses of the vessels, heat exchangers, pumps and connecting lines can be reduced.

The above content of the present invention is further described in detail with reference to the specific mode in a manner of examples below.

In the invention, an absorption ratio is defined as follows:

absorption ratio(%)=(MAL concentration before adsorption−MAL concentration after adsorption)/MAL concentration before adsorption×100% wherein, MAL is methylacrolein.

The specific names and structures of the ionic liquids used in the examples are as follows respectively:

1. Name: tetrabutylammonium hexafluorophosphate

Abbreviation: $[NC_{4,4,4,4}][PF_6]$

Molecular formula: $C_{16}H_{36}PF_6N$,

Structural formula:

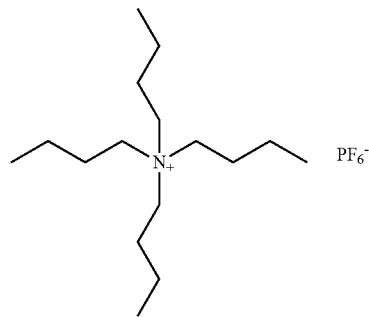

2. Name: tetrabutylphosphonium tetrafluoroborate

Abbreviation: $[PC_{4,4,4,4}][BF_4]$

Molecular formula: $C_{16}H_{36}PF_4P$,

Structural formula:

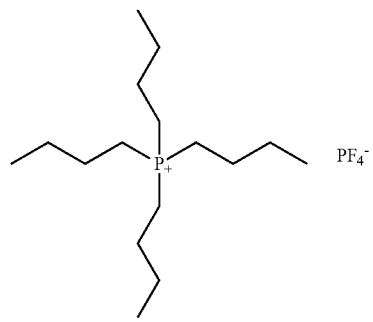

3. Name: 1-butyl-3-methylimidazolium tetrafluoroborate

Abbreviation: $[Bmim][BF_4]$

Molecular formula: $C_8H_{15}BF_4N_2$,

Structural formula:

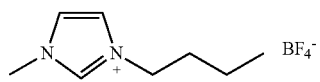

4. Name: N-butylpyridinium hexafluorophosphate
Abbreviation: [C$_4$Py][BF$_6$]
Molecular formula: C$_9$H$_{14}$BF$_6$N,
Structural formula:

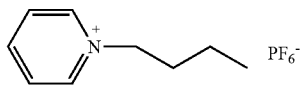

Preparation Examples of Ionic Liquids
Preparation of Tetrabutylammonium Hexafluorophosphate:

Tetrabutylammonium chloride was added into an aqueous solution with excessive amount of potassium hexafluorophosphate (molar ratio: 1/1.1) and stirred for 24 hours. After settlement, a product was separated from the reactant solution. The separated product was washed with a small quantity of water for many times until no chlorine ion was detected by a silver nitrate solution (0.1 mol/L). A product of tetrabutylammonium hexafluorophosphate was obtained after drying.

Preparation of Tetrabutylphosphonium Tetrafluoroborate:

Tetrabutylphosphonium chloride was added into an aqueous solution with excessive amount of sodium tetrafluoroborate (molar ratio: 1/1.1) and stirred for 24 hours. Then, adequate amount of methylene dichloride was added to extract the product. A mixture of the product and the methylene dichloride was washed with water until no chlorine ion was detected by a silver nitrate solution (0.1 mol/L). A product of tetrabutylphosphonium tetrafluoroborate was obtained after removing methylene dichloride in the product by rotary evaporation and drying.

Preparation of 1-butyl-3-methylimidazolium tetrafluoroborate

Methylimidazole and excessive amount of chloro-n-butane (molar ratio: 1/1.05) were reacted at 70° C. with stirring for 48 hours. Excessive of reactants were removed by rotary evaporation, thereby 1-butyl-3-methylimidazolium chloride was obtained. The obtained 1-butyl-3-methylimidazolium chloride was further added into an aqueous solution with excessive amount of sodium tetrafluoroborate (molar ratio: 1/1.1) and stirred for 24 hours. Then, adequate amount of methylene dichloride was added to extract the product. A mixture of the product and the methylene dichloride was washed with water until no chlorine ion was detected by a silver nitrate solution (0.1 mol/L). A product of 1-butyl-3-methylimidazolium tetrafluoroborate was obtained after removing methylene dichloride in the product by rotary evaporation and drying.

Preparation of N-Butylpyridinium Hexafluorophosphate

Pyridine and excessive amount of chloro-n-butane (molar ratio: 1/1.05) were reacted at 70° C. with stirring for 48 hours. Excessive of reactants were removed by rotary evaporation, thereby N-butylpyridinium chloride was obtained. The obtained N-butylpyridinium chloride was further added into an aqueous solution with excessive amount of potassium hexafluorophosphate (molar ratio: 1/1.1) and stirred for 24 hours. After settlement, a product was separated from the reactant solution. After liquid separation, the product was washed with water until no chlorine ion was detected by a silver nitrate solution (0.1 mol/L). A product of N-butylpyridinium hexafluorophosphate was obtained after removing methylene dichloride in the product by rotary evaporation and drying.

EXAMPLE 1

Methylacrolein absorption experiments were carried out by utilizing methanol, water, quaternary ammonium salt [NC$_{4,4,4,4}$][PF$_6$], quaternary phosphonium salt [PC$_{4,4,4,4}$][BF$_4$], imidazolium type ionic liquid [Bmim][BF$_4$] and pyridinium type ionic liquid [C$_4$Py][BF$_6$] as an absorbent respectively under the following conditions.

Absorption Conditions:

The gas composition: 0.22% of IB (iso-butylene), 1.51% of O$_2$, 68.11% of N$_2$, 12.30% of H$_2$O, 4.25% of CO$_2$, 1.77% of CO, 10.97% of MAL, 0.50% of MAA, 0.1% of C$_3$H$_6$O.

Flow rate of the gas: 15 ml/min
Amount of absorbent: 40 ml
Absorbent: methanol, analytical pure, Beijing Chemical Reagent Factory
Water: deionized water
Quaternary ammonium salt: [NC$_{4,4,4,4}$][PF$_6$], synthesized in lab, tested purity of 99.0%, water content ≦10000 ppm
Quaternary phosphonium salt: [PC$_{4,4,4,4}$][BF$_4$], synthesized in lab, tested purity of 99.0%, water content ≦10000 ppm
Imidazolium type: [Bmim][BF$_4$], synthesized in lab, tested purity of 99.0%, water content ≦10000 ppm
Pyridinium type: [C$_4$Py][BF$_6$], synthesized in lab, tested purity of 99.0%, water content ≦10000 ppm
Temperature 20° C., normal pressure operation Bubbling static absorption kettle absorption method: in the static absorption kettle absorption process, a gas stream was continuously fed into a solvent kettle loaded with a solvent from the bottom of the kettle and an off-gas after absorption was discharged from the top of the kettle. MAL in the gas stream was absorbed and remained in the solvent.

| | | | Comparison of absorption results | | | |
|---|---|---|---|---|---|---|
| Time (min) | Absorption ratio in methanol (%) | Absorption ratio in water (%) | Absorption ratio in [NC$_{4,4,4,4}$][PF$_6$] (%) | Absorption ratio in [PC$_{4,4,4,4}$][BF$_4$] (%) | Absorption ratio in [Bmim][BF$_4$] (%) | Absorption ratio in [C$_4$Py][BF$_6$] (%) |
| 0 | 92.26 | 92.92 | 95.13 | 94.85 | 95.70 | 95.20 |
| 20 | 91.73 | 90.35 | 95.07 | 94.06 | 95.48 | 95.08 |
| 40 | 91.35 | 86.23 | 94.81 | 94.21 | 95.31 | 94.91 |
| 80 | 90.80 | 77.76 | 94.11 | 93.67 | 94.37 | 94.30 |
| 160 | 89.16 | 62.79 | 89.94 | 89.03 | 91.93 | 91.02 |
| 280 | 86.31 | 35.32 | 88.02 | 87.30 | 88.40 | 87.91 |
| 400 | 83.90 | — | 84.17 | 83.52 | 84.61 | 84.11 |
| 520 | 81.19 | — | 80.13 | 80.05 | 80.85 | 80.54 |

Results: In this example, methylacrolein absorption experiments were carried out by using four representational ionic liquids of quaternary ammonium salt ($[NC_{4,4,4,4}][PF_6]$), quaternary phosphonium salt ($[PC_{4,4,4,4}][BF_4]$), imidazolium type ($[Bmim][BF_4]$) and pyridinium type ($[C_4Py][BF_6]$), whose cations were respectively selected from four types of cations for ionic liquid. As seen from the results listed in Table 1, all of these four ionic liquids exhibited superior absorption effects for methylacrolein.

EXAMPLE 2

Absorption Conditions
The gas composition was the same as that in example 1.
Amount of absorbent [Bmim][BF$_4$]: 20 ml
Flow rate of the gas: 15 ml/min
Temperature 20° C.
Bubbling static absorption kettle
Absorption Results:

| Time (min) | Absorption ratio in [Bmim][BF$_4$] (%) |
|---|---|
| 5 | 86.26 |
| 10 | 86.04 |
| 20 | 84.86 |
| 30 | 82.83 |
| 40 | 81.52 |
| 50 | 79.34 |
| 60 | 80.49 |
| 70 | 79.28 |

As compared with example 1, the absorption effect dropped because the addition amount of the absorbent was reduced.

EXAMPLE 3

The ionic liquid [Bmim][BF$_4$] which had absorbed methylacrolein in example 1 was subjected to desorption. After the first desorption is completer, the second absorption, the second desorption and then the third absorption in turn were carried out. The desorption method was a heating method, and the absorption conditions were the same as those in example 1.

Comparison of absorption results

| Time (min) | Absorption ratio of the first absorption (%) | Absorption ratio of the second absorption (%) | Absorption ratio of the third absorption (%) |
|---|---|---|---|
| 0 | 95.70 | 90.97 | 87.53 |
| 60 | 94.95 | 88.42 | 91.66 |
| 120 | 93.17 | 84.95 | 90.00 |
| 180 | 91.36 | 81.58 | 87.48 |
| 240 | 89.53 | 78.81 | 84.60 |
| 300 | 87.70 | 76.02 | 83.43 |
| 360 | 85.86 | 74.57 | 80.57 |
| 420 | 83.85 | 72.84 | 78.48 |
| 480 | 81.92 | 71.03 | 77.03 |
| 540 | 80.10 | 69.75 | 75.88 |

As seen from the data in the above table, the ionic liquid after regeneration still exhibit excellent absorption effect while the performances thereof were relatively stable.

EXAMPLE 4

A methylacrolein-rich gas stream was fed into a continuous absorption column containing a composite solvent of an ionic liquid and methanol (methanol accounted for 20%) which had 10 column trays and was operated at normal pressure. The continuous absorption process was as follows: the gas stream was continuously fed into the absorption column from the bottom thereof and the solvent was continuously fed into the column from the top thereof, so that a counter-current contacting absorption was carried out; the off-gas after absorption was discharged from the top of the column and the solvent after absorbing MAL was discharged from the bottom of the column. The gas temperature at inlet was 110° C. The gas composition was the same as that in example 1, and the mass flow rate was 14.56 kg/h. 30 kg/h of a solution of [Bmim][BF$_4$] and methanol at 20° C. was used to perform the absorption. The temperature at the bottom of the column was 36.6° C. and the temperature at the top of the column was 2.1° C. The overhead gas composition after the absorption was 0.02% of IB, 1.96% of O2, 89.6% of N2, 0.47% of H2O, 5.5% of CO2, 2.32% of CO, 0.006% of MAL, and trace amount of $C_3H_6O$.

By utilizing a composite solvent of an ionic liquid and methanol, it is easy to realize a continuous absorption process which exhibits better absorption effect and is stable and continuously operable.

Note: All of the above compositions are based on mass percentage.

We claim:

1. A process for absorbing methylacrolein, comprising contacting methylacrolein with an absorbent comprising an ionic liquid so as to absorb the methylacrolein with the absorbent.

2. The process as claimed in claim 1, wherein the absorbent is the ionic liquid in pure form, a mixture of the ionic liquid and an alcohol, a mixture of the ionic liquid and water, or a mixture of the ionic liquid, water and an alcohol.

3. The process as claimed in claim 1 or 2, wherein the ionic liquid is selected from the group consisting of alkyl quaternary ammonium salts, alkyl quaternary phosphonium salts, N-alkyl substituted pyridiniums, N,N'-dialkyl substituted imidazoliums, and mixtures thereof.

* * * * *